US010682512B1

(12) United States Patent
Feinstein

(10) Patent No.: US 10,682,512 B1
(45) Date of Patent: Jun. 16, 2020

(54) SYSTEM AND METHOD EMPLOYING INTERFERENTIAL ELECTRICAL STIMULATION FOLLOWING SURGERY

(71) Applicant: Feinstein Patents, LLC, Wilkes-Barre, PA (US)

(72) Inventor: Peter A. Feinstein, Palm Beach Gardens, FL (US)

(73) Assignee: Feinstein Patents, LLC, Wilkes-Barre, PA (US)

( * ) Notice: Subject to any disclaimer, the term of this patent is extended or adjusted under 35 U.S.C. 154(b) by 0 days.

(21) Appl. No.: 16/725,491

(22) Filed: Dec. 23, 2019

Related U.S. Application Data

(60) Provisional application No. 62/868,472, filed on Jun. 28, 2019.

(51) Int. Cl.
A61N 1/36 (2006.01)
A61N 1/04 (2006.01)
A61B 90/00 (2016.01)

(52) U.S. Cl.
CPC ....... A61N 1/36021 (2013.01); A61N 1/0456 (2013.01); A61B 90/39 (2016.02)

(58) Field of Classification Search
CPC ... A61N 1/36021; A61N 1/0456; A61B 90/39
USPC .......................................................... 607/46
See application file for complete search history.

(56) References Cited

U.S. PATENT DOCUMENTS

| 6,972,022 | B1* | 12/2005 | Griffin | A61B 90/39 |
| | | | | 604/112 |
| 9,067,080 | B2* | 6/2015 | Einy | A61N 1/39 |
| 10,456,573 | B1 | 10/2019 | Feinstein | |
| 2016/0030737 | A1* | 2/2016 | Gerasimenko | A61N 1/36003 |
| | | | | 607/48 |
| 2016/0325071 | A1* | 11/2016 | Shambroom | A61M 21/00 |

OTHER PUBLICATIONS

Gregg J. Jarit et al., "The Effects of Home Interferential Therapy on Post-Operative Pain, Edema, and Range of Motion of the Knee", Clinical Journal of Sports Medicine, vol. 13, No. 1, 2003.

* cited by examiner

Primary Examiner — Amanda K Hulbert
Assistant Examiner — Philip C Edwards
(74) Attorney, Agent, or Firm — Forge IP, PLLC

(57) ABSTRACT

An interferential current therapy kit for treatment of a patient following an orthopedic surgery, includes, within a container for facilitating the distribution and transport of the kit, one or multiple control units including a stimulation power supply and a plurality of electrodes configured to be in electrical communication with the stimulation power supply. The plurality of electrodes are configured to be disposed on an epidermis of the patient and arranged to supply transcutaneous electrical impulses to a therapeutic target area when supplied power by the stimulation power supply employing an interferential current therapy technique. The kit also includes an electrode placement aid adapted to assist the health care provider and team, and the patient with placement of the plurality of electrodes with respect to the site of the previous orthopedic surgery, thereby increasing a likelihood of efficacious and safe placement of the plurality of electrodes.

22 Claims, 6 Drawing Sheets

SYSTEM AND METHOD EMPLOYING INTERFERENTIAL ELECTRICAL STIMULATION FOLLOWING SURGERY

FIELD OF THE INVENTION

The invention relates to a system and method employing the use of an electrical stimulator, such as an Interferential Current (IFC) device, or other type of deep penetration electrical stimulation that is non-invasive and external (i.e., transcutaneous), for treatment following orthopedic surgeries. More specifically, the invention relates to a treatment system and method of the type described for pain management and/or reducing edema following knee arthroplasty surgery.

BACKGROUND OF THE INVENTION

The theory of electrical stimulation therapy for pain control has been studied at significant length since it was initially theorized. Historically, the use of electrical properties to control pain dates back to 46 AD when torpedo fish were used to treat headache and gout. The theory behind the effectiveness of the use of electrical stimulation for pain has been described as the gate theory of pain modulation, which describes how pain stimulation can be blocked from reaching the brain by other signals. This theory has provided the bases for pain management with electrical stimulation using different modalities. In the 1950s, the use of interferential current therapy (IFC) was developed to provide dual current therapy to provide deeper tissue penetration to allow for improved pain relief.

In the field of orthopedic surgery, several studies have compared the use of electrical stimulation therapy for patient pain relief with differing results. Two systematic reviews were done comparing use of transcutaneous electrical nerve stimulation (TENS) as a possible adjunct after total knee arthroplasty (TKA). Both studies found significant improvement of pain scales and active knee range of motion.

More specifically, IFC therapy has also been compared to both TENS and placebo for pain relief. When compared to TENS for back pain, there are conflicting results. Some studies indicate overall pain improvement but no difference between modalities. Another study found IFC to be more effective in treating chronic low back pain due to deeper tissue penetration. The author of this patent application is an Orthopedic Surgeon, and has compared TENS unit treatment to IFC treatment in clinical practice with findings of IFC use to be far more effective than TENS for treatment of muscular and neurogenic pain.

One study out of Kerlan-Jobe Orthopaedic clinic in 2001 compared IFC therapy to placebo for post-operative pain, edema and range of motion after ACL, meniscectomy or knee chondroplasty. In this randomized, double-blind, placebo controlled prospective study, patients were treated post-operative with IFC therapy providing therapeutic or placebo electrical stimulation. In the study, all IFC subjects reported significantly less pain and greater range of motion for all reviewed time points.

The present invention improves upon the Kerlan-Jobe study by providing for a system and method employing IFC therapy that may be used by patients following orthopedic surgeries, for example, following knee arthroplasty surgery. The present invention provides for improved patient outcomes, which result in shorter hospital stay, reduced use of opioid medication and decreased need for manipulation under anesthesia.

SUMMARY OF THE INVENTION

Accordingly, one object of the present invention is to provide a system and method that results in reduced pain, increased range of motion and/or reduced edema following orthopedic surgery.

Such a system and method allows for the present invention to be safely implemented and used in the immediate post-operative care timeframe (whether inpatient or outpatient) upon completion of the surgical procedure, by allowing the surgeon, the surgeon's supporting personnel, and the patient's care team (such as nurses, surgical techs, physicians assistants, physical therapists, etc.) to safely and consistently apply and use the invention.

It is another object of the present invention to provide such a system and method that may be safely employed by the patients by themselves or together with healthcare personnel after having been released from the hospital and/or health care facility.

It is also an object of the present invention to provide such a system and method that facilitates use by the patient and/or the surgeon and the patient's health care team, and that minimizes the chances of accidental or inadvertent misuse and/or harm to the patient.

At least some of these, and other, objects may be achieved in accordance the invention by provision of a kit that may be provided to a patient, the surgeon and patient's healthcare team, the operating room, the hospital and/or the hospital supply chain/vendors, with such a kit incorporating all items needed to employ the inventive system and method to the patient.

More specifically, in accordance with a first aspect of the present invention, an interferential current therapy kit for treatment of a patient following an orthopedic surgery, comprises, within a container for facilitating the distribution and transport of the kit, one or more control units comprising a stimulation power supply and a plurality of electrodes configured to be in electrical communication with the stimulation power supply. The plurality of electrodes are configured to be disposed on an epidermis of the patient and arranged to supply transcutaneous electrical impulses to a therapeutic target area when supplied power by the stimulation power supply. The plurality of electrodes comprises at least two electrodes adapted to supply transcutaneous electrical impulses at two different frequencies, the transcutaneous electrical impulses provided at two different frequencies adapted to give rise to at least one beat impulse having an interference frequency. The kit also includes an electrode placement aid adapted to assist the surgeon, the patient, and the health care team with placement of the plurality of electrodes with respect to the site of the previous orthopedic surgery, thereby increasing a likelihood of efficacious placement of the plurality of electrodes.

In some embodiments, the electrode placement aid comprises a marking instrument. In certain of these embodiments, the marking instrument comprises an ink marker that makes ink markings on the patient which may last for days or up to 6 weeks (6 weeks being the usual completion timeframe for post op full recovery in the acute rehab of a knee arthroplasty) or longer.

In some embodiments, the electrode placement aid comprises a template. In certain of these embodiments, the template comprises a drape that includes at least one of openings and markings showing a relative intended placement of the plurality of electrodes with respect to anatomical structure. The template size and configuration chosen in the pre or post op planning process as being appropriate for an individual patient's anatomy can then be converted into or made into a drape or fabric for actual treatment that incorporates the electrodes directly into the template itself, with the patient specific configuration of the template then functioning as the actual treatment targeting device or mechanism. The treatment drape or fabric template including the electrodes can be adjustable thru folding, cutting, use of elastic bands, and other mechanisms obvious to those familiar with the art, so that manufacture of the template can be generic, yet the generic treatment template or "drape" can be adjusted to the unique anatomy of the individual patient.

In some embodiments, the electrode placement aid comprises a measuring device. In certain of these embodiments, the measuring device comprises at least one of a ruler and a tape measure.

In some embodiments, the electrode placement aid comprises an x-ray marker. In certain of these embodiments, the x-ray marker comprises at least one of the following: radiology tape with metal beads, radiology tape with a central strip of radiopaque marker and other radiology devices which are radiopaque, but are not metallic in nature.

In some embodiments, the electrode placement aid comprises an imaging device adapted to assist with electrode placement. In certain of these embodiments, the imaging device is adapted to interface with a mobile phone or tablet.

In some embodiments, the electrode placement aid is adapted to interface with markings created on a body of the patient. In some embodiments, the control unit further comprises at least one sensor adapted to provide sensor feedback indicative of a patient parameter derived from the patient. In some embodiments, the kit further comprises a plurality of wire leads adapted to connect the control unit with the plurality of electrodes.

In some embodiments, the plurality of electrodes comprises: a first electrode adapted to supply transcutaneous electrical impulses at a first frequency and a second electrode adapted to supply transcutaneous electrical impulses at a second frequency different than the first frequency, the transcutaneous electrical impulses provided at the first and second frequencies adapted to give rise to a first beat impulse having a first interference frequency; and a third electrode adapted to supply transcutaneous electrical impulses at a third frequency and a fourth electrode adapted to supply transcutaneous electrical impulses at a fourth frequency different than the third frequency, the transcutaneous electrical impulses provided at the third and fourth frequencies adapted to give rise to a second beat impulse having a second interference frequency.

In accordance with another aspect of the present invention, an interferential current therapy kit for treatment of a patient following an orthopedic surgery comprises a control unit or units comprising a stimulation power supply and a plurality of electrodes configured to be in electrical communication with the stimulation power supply. The plurality of electrodes are configured to be disposed on an epidermis of the patient and arranged to supply transcutaneous electrical impulses to a therapeutic target area when supplied power by the stimulation power supply. The plurality of electrodes comprises at least two electrodes adapted to supply transcutaneous electrical impulses at two different frequencies, the transcutaneous electrical impulses provided at two different frequencies adapted to give rise to at least one beat impulse having an interference frequency. The kit also includes an electrode placement aid adapted to assist the patient with placement of the plurality of electrodes with respect to a site of the previous orthopedic surgery, the electrode placement aid comprising at least one of the following: a marking instrument; a template; a measuring device; an x-ray marker; and an imaging device.

In some embodiments, the electrode placement aid comprises at least two of the following: a marking instrument; a template; a measuring device; an x-ray marker; and an imaging device. In certain of these embodiments, the electrode placement aid comprises at least three of the following: a marking instrument; a template; a measuring device; an x-ray marker; and an imaging device.

In some embodiments, the control unit further comprises at least one sensor adapted to provide sensor feedback indicative of a patient parameter derived from the patient.

In some embodiments, the plurality of electrodes comprises: a first electrode adapted to supply transcutaneous electrical impulses at a first frequency and a second electrode adapted to supply transcutaneous electrical impulses at a second frequency different than the first frequency, the transcutaneous electrical impulses provided at the first and second frequencies adapted to give rise to a first beat impulse having a first interference frequency; and a third electrode adapted to supply transcutaneous electrical impulses at a third frequency and a fourth electrode adapted to supply transcutaneous electrical impulses at a fourth frequency different than the third frequency, the transcutaneous electrical impulses provided at the third and fourth frequencies adapted to give rise to a second beat impulse having a second interference frequency.

The invention and its particular features and advantages will become more apparent from the following detailed description considered with reference to the accompanying drawings.

DETAILED DESCRIPTION OF THE INVENTION

Figure 1:
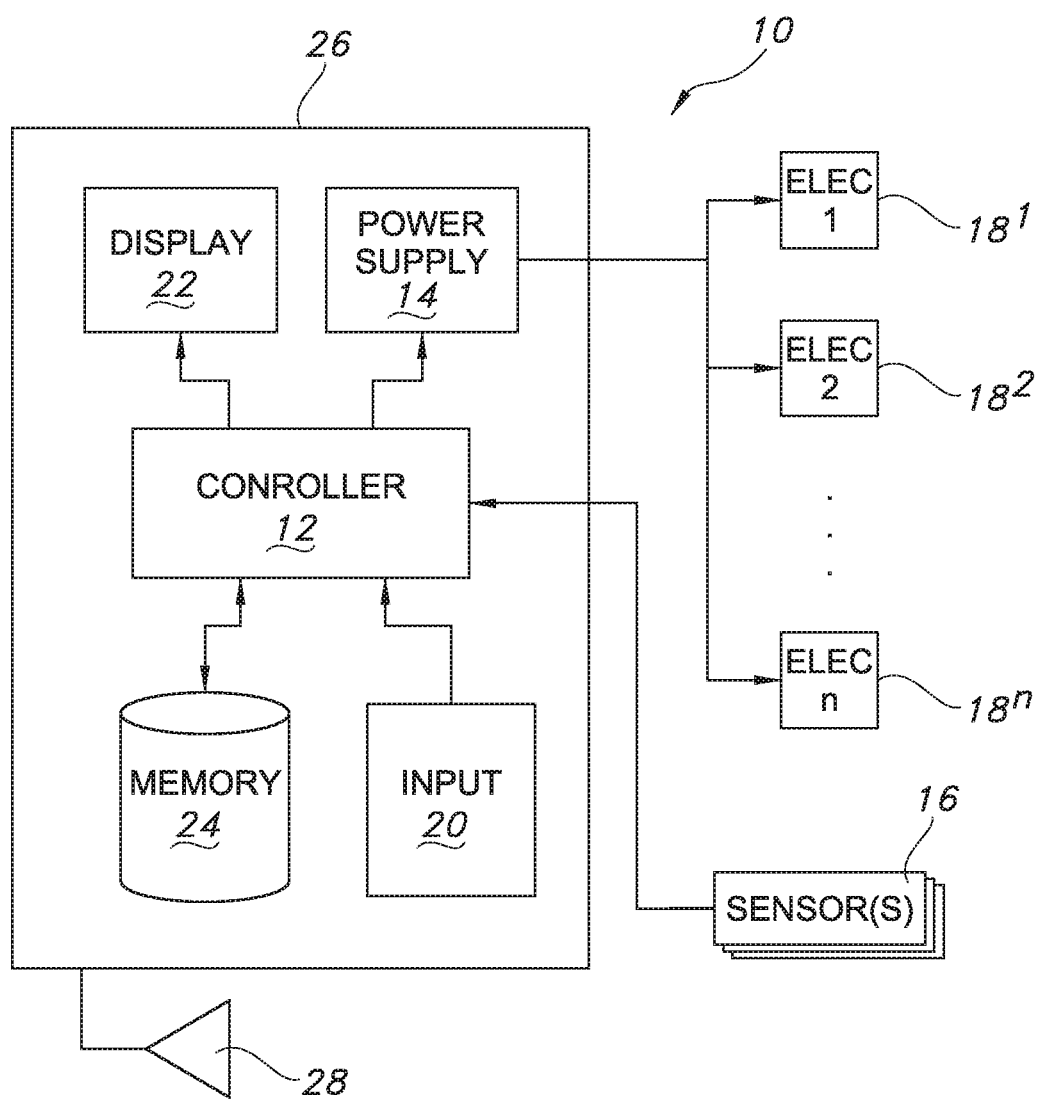
FIG. 1 is a block diagram schematically illustrating a basic device employing interferential current (IFC) therapy together with targeting capabilities to ensure that the stimulating currents are directed to the appropriate areas of the body to achieve the desired results, according to an exemplary embodiment of the present invention.

Referring first to FIG. 1, shown is a system (10) employing the use of an electrical stimulator, such as an Interferential Current (IFC) device, or other type of deep penetration electrical stimulation that is non-invasive and external (i.e., transcutaneous), that may be used in conjunction with the inventive system and method for treatment following orthopedic surgeries. The system (10) includes a controller (12) and a stimulation power supply (14) in communication with the controller (12).

The system (10) also includes a plurality of electrodes ($18^1, 18^2 \ldots 18^n$) in electrical communication with the stimulation power supply (14). The plurality of electrodes ($18^1, 18^2 \ldots 18^n$), the location of which are described further below, are arranged to supply electrical impulses that cause activation of sympathetic and/or parasympathetic nerves when supplied power by the stimulation power supply.

As used herein, the terms "electrode" and "electrodes" encompass electrical coils, electrical plates, electrical conductors, conductive fabrics and gels, and any other conductive materials and devices. Exemplary electrodes that have been found to provide suitable results in connection with the present invention are those distributed by Keystone Rehab Products, LLC of Kingston, Pa. under the QUATRODE™ brand, which conveniently incorporate four separate electrodes (the relevance of which is discussed below) into a single patch.

The controller (12) causes the stimulation power supply (14) to supply power to the plurality of electrodes ($18^1, 18^2 \ldots 18^n$) in response to a command from the controller (12) pursuant to manual user input and/or a program stored thereon. As is explained in more detail below, the power supplied to the plurality of electrodes ($18^1, 18^2 \ldots 18^n$) is such that transcutaneous electrical impulses are created in order to cause sympathetic and/or parasympathetic nerve activation.

The system (10) also includes an input mechanism (20), such as a graphical user interface, microphone for receiving voice commands, keyboard, joystick, or the like, which allows the user to enter control parameters and the like. As examples, input mechanism (20) may include a button or other type of controller to turn the device on or off manually, to trigger activation of sympathetic and/or parasympathetic nerves and/or to allow the user to vary the intensity of the treatments.

In some embodiments, the system may optionally include a sensor (16) providing sensor feedback to the controller (12), and the controller (12) may cause the stimulation power supply (14) to supply power to the plurality of electrodes ($18^1, 18^2 \ldots 18^n$) based, at least in part, on the sensor feedback received from the sensor (16). For instance, the sensor feedback may be indicative of a level of edema present in surgical area, which information may be helpful in tracking progress of past and/or current treatments and/or in helping to define the parameters of current and/or future treatments, such as for example, by varying an intensity of the treatments.

In some embodiments, the system (10) also includes a display (22) to provide visual and/or auditory output to a user of the system (10). The display (22) may also present the user with other helpful information, such as previously loaded data for the patient, or current edema levels and previously recorded edema levels, prior to the supply of power to the electrodes ($18^1, 18^2 \ldots 18^n$), such that a comparison can be made to determine whether the electrical stimulus is actively affecting the targeted pathway.

The system (10) further includes a memory (24), which allows the system to store various parameters that may be employed by the controller (12), or data recorded prior to and/or during the supply of power to the electrodes ($18^1, 18^2 \ldots 18^n$).

In some embodiments the system further includes the ability to transmit information and data obtained through the Internet or other mechanism to remote or off site locations for evaluation by the treating physician, and monitoring of data garnered during or after the treatment, or for incorporation into EMRs, or for telehealth applications.

The controller (12), stimulation power supply (14), input mechanism (20), display (22), memory (24) and an optional antenna (28) for wireless communication may be (but are not necessarily) contained in a housing (26), as should be apparent to those skilled in the art. Various types of connectors may be provided on the housing to allow for connection of the electrodes ($18^1, 18^2 \ldots 18^n$), the sensor (16), or various other devices (e.g., mobile phones, tablets, smart watches, etc.), as should also be apparent to those skilled in the art. This connection may be wired (which requires grounding in a manner similar to that of an electrocoagulation device), or wireless, as further described below.

As will be explained in greater detail below with respect to the exemplary treatment system and method following knee arthroplasty surgery, specific targeting for the IFC impulses is important in the context of the present invention so as to avoid the potential for harm to the patient (as has been known to happen, for example, if the electrodes are placed too close to a metal implant), as well as to increase the efficacy of the treatment. Moreover, since the inventive system and method is intended to be employable by the healthcare team (inpatient or outpatient), as well as by the patient himself/herself after being discharged from the hospital or medical facility where the surgery is performed, an electrode placement aid is provided to the patient, for example, as part of an overall kit provided to the patient (as discussed in more detail below).

Although the use of various types of deep penetration electrical stimulation that are non-invasive and external (i.e. transcutaneous) is contemplated, the presently discussed exemplary embodiment employs interferential current (IFC) technology.

In general, IFC therapy utilizes two medium frequency currents which pass through the tissues simultaneously. They are set up so that their paths cross; and in simple terms they interfere with each other. This interference gives rise to an interference or beat frequency, which has the characteristics of low-frequency stimulation. The exact frequency of the resultant beat frequency can be controlled by the input frequencies. For example, if one current were at 4000 Hz and the other current at 3900 Hz, the resultant beat frequency would be at 100 Hz.

Thus, the basic principle of IFC therapy is to utilize the strong physiological effects of the low frequency electrical stimulation of muscle and nerve tissues at sufficient depth, without the associated painful and somewhat unpleasant side effects of such stimulation. The medium frequency currents penetrate the tissues with very little resistance, whereas the resulting interference current (low frequency) is in the range that allows effective stimulation of the biological tissues. The resistance (impedance) of the skin is inversely proportional to the frequency of the stimulating current.

In other words, the lower the stimulation frequency, the greater the resistance to the passage of the current, so more discomfort is experienced. The skin impedance at 50 Hz is approximately 3200 ohms, whilst at 4000 Hz, it is reduced to approximately 40 ohms. The result of applying this latter frequency is that it will pass more easily through the skin and any other tissues before hitting the target tissue or organ with a therapeutic beat frequency resulting in the desired physiologic response from the target organ or tissue, requiring less electrical energy input to the deeper tissues, giving rise to less discomfort.

Figure 2:
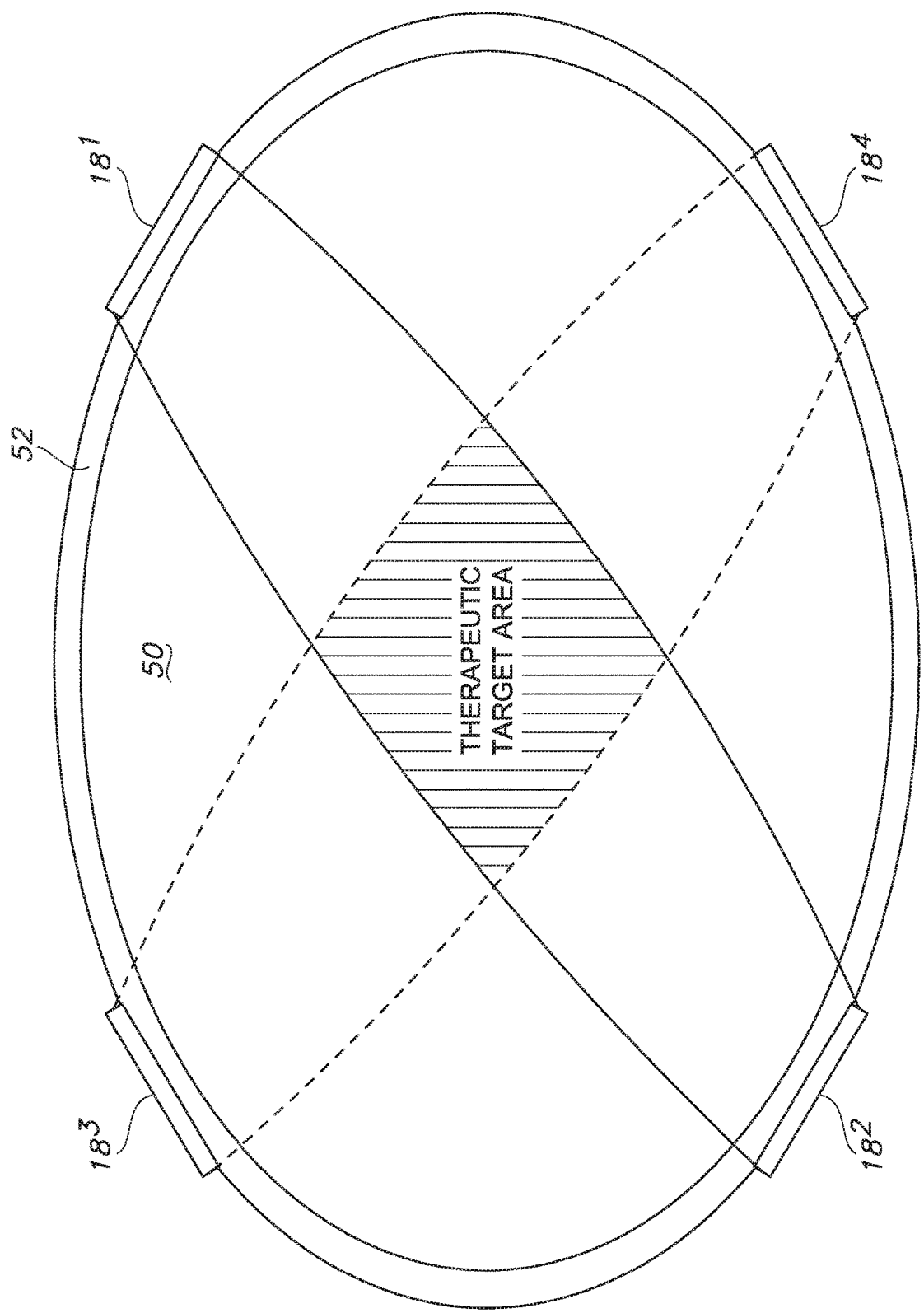
FIG. 2 is schematic view illustrating rudimentary operational characteristics of the device shown in FIG. 1.

Referring now to FIG. 2, an exemplary arrangement of electrodes employing IFC therapy is shown applied to the epidermis (52) of a patient (50). In this example, a first pair of electrodes ($18^1$, $18^2$) supplies transcutaneous electrical impulses at a first frequency (represented by solid lines) and a second pair of electrodes ($18^3$, $18^4$) supplies transcutaneous electrical impulses at a second frequency (represented by dashed lines) different than the first frequency. The transcutaneous electrical impulses provided at the first and second frequencies giving rise to a beat impulse in a Therapeutic Target Area (located at the position shown in FIG. 2 where the area defined by solid lines and the area defined by dashed lines overlap) having an interference frequency. The beat impulse results in activation of the sympathetic and/or parasympathetic nerves.

The beat impulse is controlled depending on the type of nerve/tissue/organ to be stimulated, as well as, optionally, on real-time feedback of the elicited response. For example, it has been found that beat impulses having a frequency in the range of from 1-5 Hz may provide desirable stimulation properties for sympathetic nerves, beat impulses having a frequency in the range of from 10-150 Hz may provide desirable stimulation properties for parasympathetic nerves, beat impulses having a frequency in the range of from 10-50 Hz may provide desirable stimulation properties for motor nerves, beat impulses having a frequency in the range of from 90-100 Hz may provide desirable stimulation properties for sensory nerves, beat impulses having a frequency in the range of from 90-150 Hz may provide desirable stimulation properties for nociceptive fibers, and beat impulses having a frequency in the range of from 1-10 Hz may provide desirable stimulation properties for smooth muscle. As will be recognized, other types of nerves/tissues/organs may respond to other beat impulse frequencies.

As has been recognized, nerves will sometimes acclimate to a constant signal. Accordingly, in some embodiments, the electrodes vary the beat frequency, either automatically or upon user input from a medical practitioner, to produce a frequency "sweep" that avoids this problem.

Figure 3:
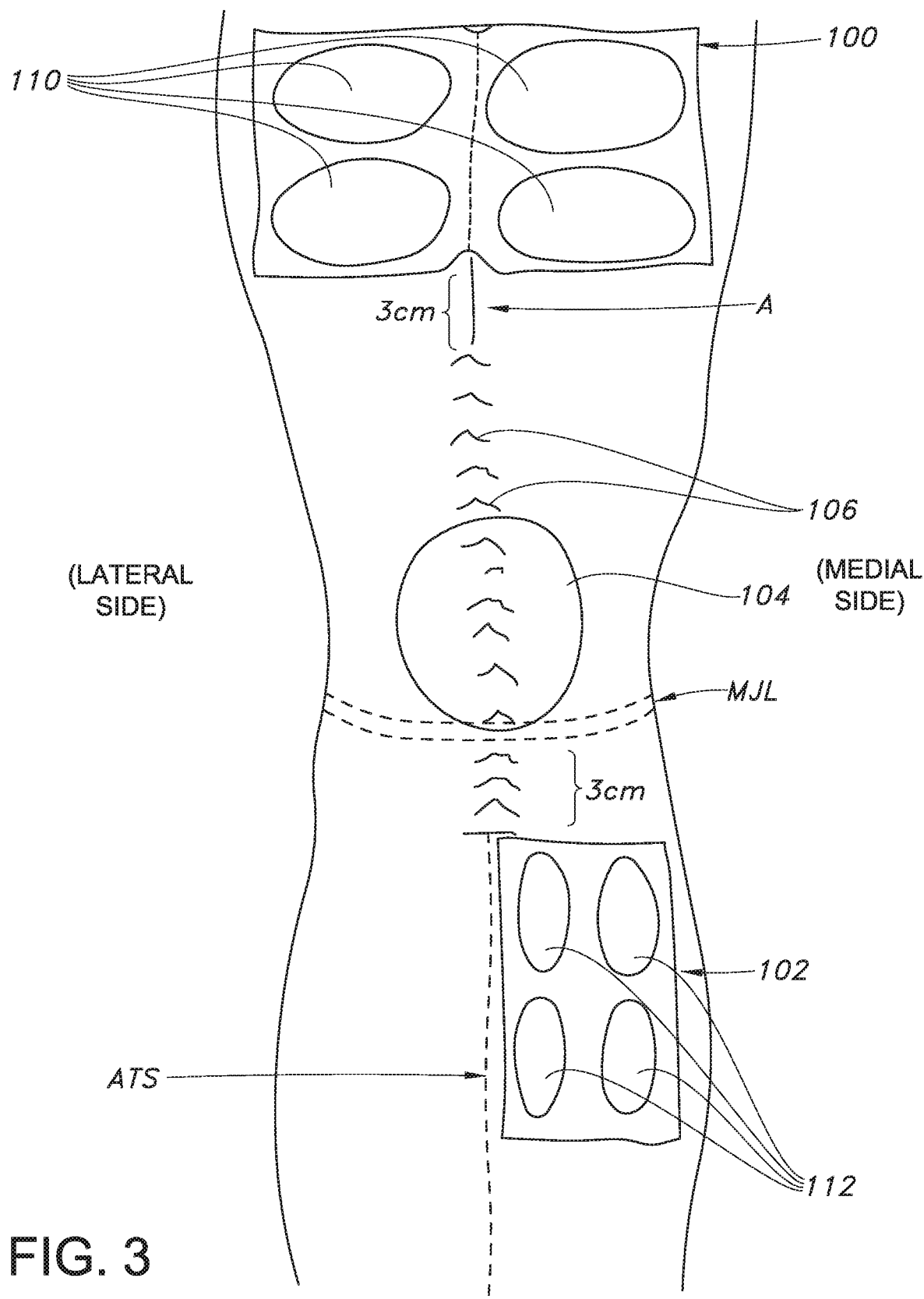
FIG. 3 is a schematic views illustrating a basic exemplary option for the placement on a patient of the electrodes of the device shown in FIG. 1, particularly for treatment following knee arthroplasty surgery.

Referring now to FIG. 3, an exemplary system and method employing the use an Interferential Current (IFC) device is shown, specifically configured for pain management, increasing range of motion and/or reducing edema following knee arthroplasty surgery. It should be understood that the term "knee arthroplasty surgery" is used herein rather than the term "total knee replacement surgery" because there are now many variations of partial knee replacements, e.g. medial compartment partial knee replacement, lateral compartment partial knee replacement, patellofemoral partial knee replacement, etc., in addition to a total knee replacement, and it is intended that the exemplary embodiment of the present invention shown in FIG. 3 can be used following any of such surgeries.

As can be seen, the exemplary embodiment shown in FIG. 3 employs two sets of electrodes, each set of electrodes disposed on a single pad (100, 102), and each set consisting of four electrodes (110, 112). One pad (100) carrying a set of electrodes (110) is positioned above the patella (104) of the knee on the patient's thigh, while the other pad (102) carrying the other set of electrodes (112) is positioned below the patella (104) of the knee on the patient's calf.

The precise types and sizes of the thigh electrodes may vary based on, for example, the size of the patient. However, it has been found that the "large" (i.e., 6.75 inches; 17 cm) QUATRODE™ brand electrode pads distributed by Keystone Rehab Products, LLC of Kingston, Pa. may provide desirable results for at least some patients.

As shown, the thigh electrodes (110) may be centered on the incision (106) created during the knee arthroplasty surgery, and positioned about 3 cm proximal to the end of the incision (as indicated by centerline A). While this placement has been shown to produce acceptable results, some variance is possible. For example, positioning the electrodes 2 cm, or even more, off the centerline (A) of the incision (in either the medial or lateral direction) has also been found to produce acceptable results. Similarly, positioning the electrodes 1 cm, or even more, closer or further from the proximal edge of the incision (i.e., such that they are from 2 cm-4 cm proximal to the proximal edge of the incision) has also been found to produce acceptable results.

As with the thigh electrodes, the precise types and sizes of the calf electrodes may vary based on, for example, the size of the patient. However, it has been found that the "medium" (i.e., 4.50 inches; 11 cm) QUATRODE™ brand electrode pads distributed by Keystone Rehab Products, LLC of Kingston, Pa. may provide desirable results for at least some patients.

As shown in FIG. 3, the calf electrodes (112) may be placed on the medial portion of the patient's calf generally parallel to, and alongside, the anterior tibial spine (ATS) of the patient, and about 3 cm below the medial joint line (MJL). While this placement has been shown to produce acceptable results, some variance is possible. For example, positioning the electrodes such that the edge thereof is 2 cm, or even more, off the anterior tibial spine (ATS) (in either the medial or lateral direction) has also been found to produce acceptable results. Similarly, positioning the electrodes 1 cm, or even more, closer or further from the medial joint line (MJL) (i.e., such that they are from 2 cm-4 cm distal to the medial joint line) has also been found to produce acceptable results.

Figure 4:
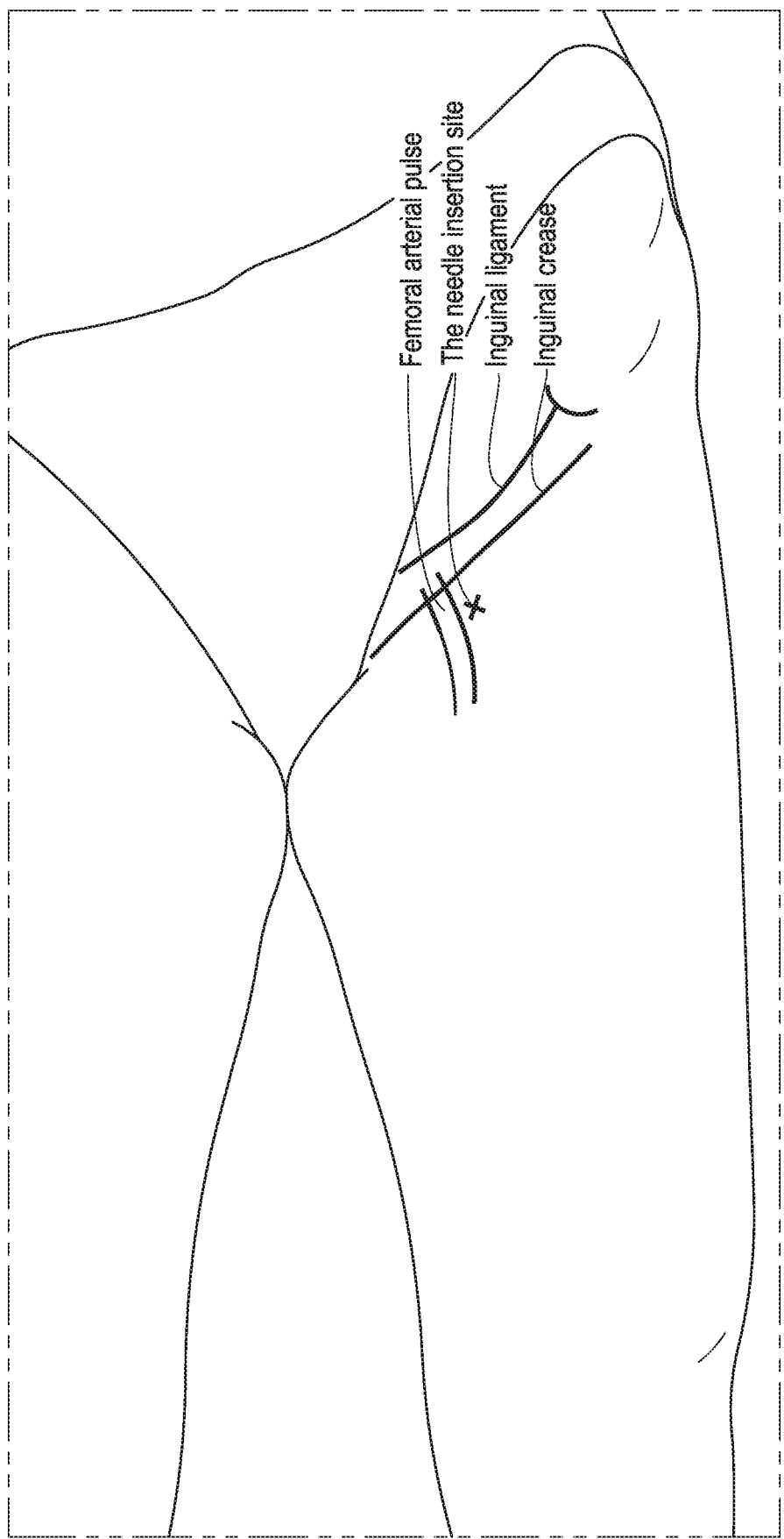
FIG. 4 is a schematic view illustrating an exemplary methodology for targeting a femoral nerve or adductor block for regional anesthesia.

Multiple other options for electrode placement that will be effective are derived from the relevant anatomy used by anesthesia to administer regional block anesthesia such as is currently used for knee replacement pain control. Examples would include, but not be limited to, femoral nerve block by the electrodes being placed which would allow for a set of electrodes to be placed more medially. With respect to FIG. 4, for example, shown is a schematic illustration of a femoral nerve or adductor block for regional anesthesia (which may be done with or without using ultrasound targeting) with the needle injection site marked with a permanent marker or the like.

This would allow one to prep over the marking of the injection site for surgery, and a proximal quatrode to be centered over the mark, with the center of the quatrode being on the mark. In this case, the overall system and kit of the present invention would essentially be functioning as an ongoing intermittent regional block that is electrical in nature, as opposed to when the medication in the regional block itself wears off after anywhere from 6 to 24 hours.

Such a block can also be achieved, for example, by positioning a thigh set of electrodes to also influence the posterior innervation to the leg. Multiple sets of electrodes can be incorporated in a circumferential fashion on the thigh at the appropriate level—once again, using targeting mechanisms already described by me as an IFC tourniquet-like device. (See, for example, FIG. 5B and accompanying text of my recently issued U.S. Pat. No. 10,456,573, which is hereby incorporated by reference herein).

The positioning also takes into account areas to be avoided, in addition to electrodes being placed too close to the implant (and then causing skin aggravation by scattering of the currents so that they may become too strong in an area and cause burns or other complications). One of the areas to be avoided by using the kit and application protocol would be to avoid the posterior calf and popliteal area to be sure the system does not cause a DVT.

Another area that the system and kit by targeting a uniform consistent application would avoid, would be the lateral knee area in the area of the fibular head and both the deep and superficial branches of the peroneal nerve so that the IFC current has no chance of causing a transient or worse peroneal nerve palsy or dropped foot.

As mentioned above, since the inventive system and method is intended to be employable by the healthcare team (inpatient or outpatient), as well as by the patient himself/herself after being discharged from the hospital or medical facility where the surgery is performed, an electrode placement aid is provided to the patient, for example, as part of an overall kit provided to the patient.

Figure 5:
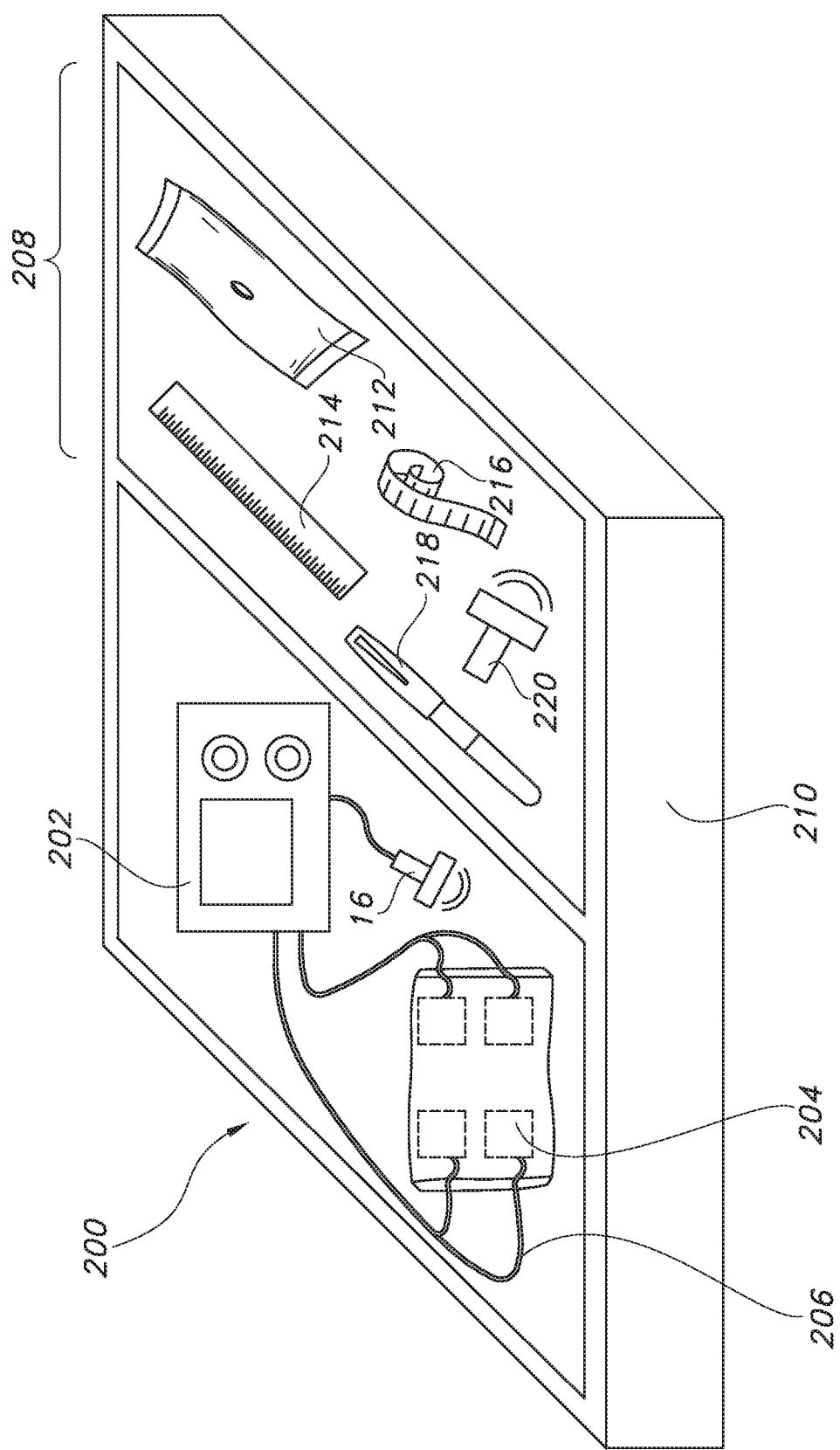
FIG. 5 is a schematic view of an exemplary kit employing the use of an electrical stimulator, such as an Interferential Current (IFC) device, or other type of deep penetration electrical stimulation that is non-invasive and external (i.e., transcutaneous), for treatment following orthopedic surgeries.

Such an exemplary kit (200), an example of which is shown in FIG. 5, may include one or multiple control units (202), which may include, for example, some or all of the components disposed within the housing (26) of FIG. 1. For example, the control unit (202) may include the controller (12), the power supply (14), the input (20), the memory (24) and the wireless antenna (28), if provided. Additionally, the kit (200) includes a plurality of electrodes (204), which may or may not be disposed on common pads, as described in more detail above, as well as any necessary wire leads (206) for connecting the electrodes to the control unit (202). The kit (200) may also include one or more sensors (16) providing sensor feedback to the control unit (202), as described above. Additionally, of critical importance given the nature of the kit (200) for home use, one or more electrode placement aids (208) are also provided in the kit (200).

In order to facilitate distribution and transportation of the kit (200), as well as to ensure that all necessary components are included, the kit is provided in a container (210), such as a box, a bag, a tray or the like. A plurality of different kits may be produced having different components, depending on such factors as the type of surgery having been performed, the size of the patient, etc. Moreover, the control unit/IFC generating device (202) contained in the kit (200) is preferably already programmed for efficacy and safety of the power supply for the electrodes and the fields that result, either by the manufacturer, or by the health care team prior to the patient's surgery. As such, little or no input by the patient or ancillary members of the treatment team is necessary during inpatient treatment or once in the home environment, thereby reducing the chances of injury caused by accidental misuse.

Figure 6:
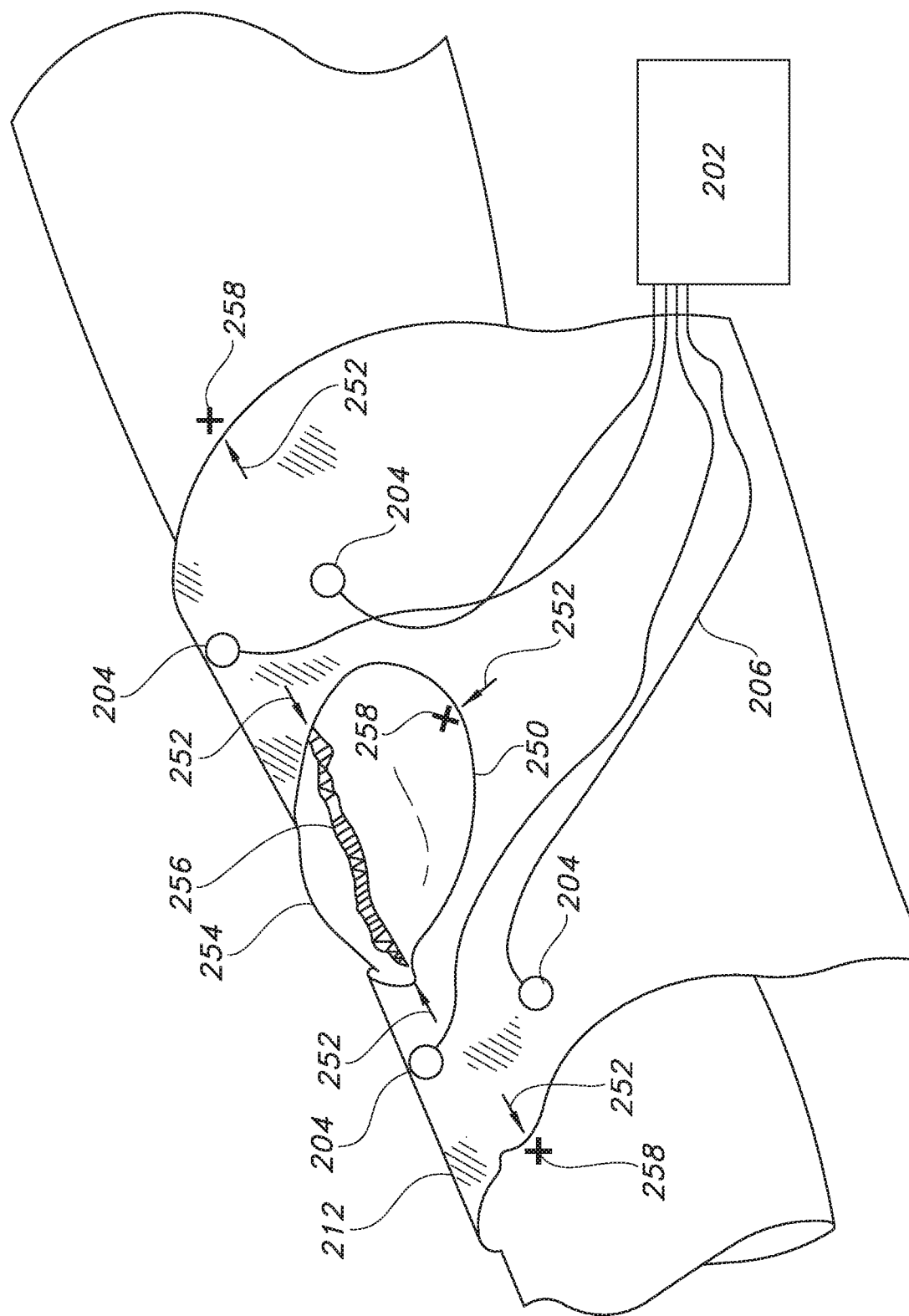
FIG. 6 is a schematic view showing in more detail an exemplary template that may be employed in connection with the inventive kit illustrated in FIG. 5

The electrode placement aid (208) may take any of various forms. For example, referring specifically to FIG. 6, the electrode placement aid (208) may take the form of a template, drape or the like that may include one or more openings (250) and/or markings (252) showing the relative intended placement of the electrodes with respect to anatomical structure (254), an incision (256) and/or markings (258) made on the patient. Such a template, drape or the like is collectively referred to herein as a template (212). The template (212) may incorporate the electrodes (204) as part of its structure and/or be constructed so as to be applied directly to the patient as part of the immediate post-operative dressing (as seen, for example, with dressing and drain systems, including the PREVENA™ incision management system).

As another example of the electrode placement aid (208), a measuring device (214) such as a ruler or tape measure may be provided or incorporated into, or directly attached to the quatrode, along with instructions and/or diagrams or the like detailing measurements and relative positioning of the electrodes with respect to anatomical structure, incisions, markings (e.g., drawn on the patient with permanent marker), etc.

Various x-ray markers (216) may be incorporated into the template or quatrode assembly to be used as targets for positioning or to verify position after deployment, but before turning on the device. Regarding x-ray, these may be in the nature of radiology tape with metal beads, or radiology tape with a central strip of radiopaque marker or other radiology devices which are radiopaque, but are not metallic in nature. Such markers or measuring devices can be used based on established special relationships to remove and replace electrodes over time so that the skin is not irritated by leaving the electrodes and the adhering backing of the electrodes for too long in one place.

A marking device (218), such as a permanent ink marking pen may be part of the kit to be used to provide an outline or a memory graphic or lines to guide the placement of the quatrode or electrode to be reattached in terms of skin care, with the electrode being placed within the outline.

The electrode placement aid (208) may also take the form of an imaging device (220), such as a sensor provided in addition or instead of the aforementioned feedback sensor (16), which is useable by the patient in the home environment. Examples of such imaging devices (220) are becoming more common, and may for example, take the form of a sensor that may be plugged into, for example, a mobile phone or other mobile device. One specific example of such a device, currently being distributed by Butterfly Networks, Inc. under the name Butterfly iQ, is an ultrasound imaging device that is a direct connect to the mobile phone. This system, which may be used as part of a targeting combination with an IFC device, allows the IFC device to be positioned when the metal of the replacement is shown on the ultrasound, and may also be used to correlate device electrode placement with the neurovascular bundles being injected by the anesthesiologist for the nerve blocks.

Moreover, when the electrode placement aid (208) is a mobile device app, additional features for targeting and transferring data may be employed. For example, a mobile phone may be used to take a photograph of the freshly closed post op wound (for size and length measurements). The app then processes this photo data and returns a picture for the surgeon (and team) that describes the landmarks previously mentioned and shows where the electrodes are to be placed, as well as their distance from the wound and other structures. This information may then be stored in the app and subsequently transmitted to the patient's individual electrical medical record (EMR) for use by other members of the team, such as the physical therapist, to replace or reposition the electrodes for subsequent treatments if the original positioning is lost or altered (i.e., to provide a "photographic/picture" targeting mechanism). This then helps to cover all the variations of incisions that are currently being used (e.g., mini incisions, anterior standard incisions, vastus splitting incisions, partial TKR incisions (size) versus complete tricompartmental TKR's, robotic surgery associated incisions, etc.) to be specific for that particular patient as to how the size of the wound gets incorporated into the determination as to how close the electrodes are placed to the fresh wound post op.

The app (or any of the targeting devices already described) preferably also has an algorithm incorporated that includes the size of the prosthesis into the calculation of the size, location and positioning of the electrodes associated with the targeting mechanism. In this regard, joint replacements are manufactured in standard sizes by a multitude of orthopedic implant providers that more or less accommodate the variation in the size of each patient's bone. The decision of type and size of implants available for use by the surgeon thus results in innumerable options. For example, one well-known implant manufacturer makes multiple standardized implants (e.g., male-small, medium, large/female-small, medium, large) for which the sizes relate to each of the femoral and tibial replacements, thus resulting in a minimum of nine different variations of size of the replacement used for each sex (e.g., large femoral component may match a medium tibial component).

Although the exemplary use for the invention has been described herein for knee arthroplasty surgery, it will be ascertainable to those of skill in the art that such use and safe application of the invention's systems and methods can be applied to, and modified to be employed in, many other types of orthopedic surgery, including but not limited to, other types of surgery of the knee (arthroscopy, ligament reconstructions and the like), as well as shoulder surgeries (such as shoulder replacements, shoulder arthroscopy and the like) hip surgeries (such as hip replacements and arthroscopies), and elbow, hand, ankle, foot or other musculoskeletal/extremity surgeries.

Placement of the electrodes may be varied depending on the particular type of surgery performed. For example, while the exemplary electrode placement locations described in detail above in connection with knee arthroplasty surgery may also be appropriate for other types of knee surgeries, other placement locations may instead be used as appropriate, such as those placement locations described by Jarit et al. in a paper entitled "The Effects of Home Interferential Therapy on Post-Operative Pain, Edema, and Range of Motion of the Knee" published in the Clinical Journal of Sports Medicine (2003; 13:16-20), the entirety of which is hereby incorporated herein by reference. For surgeries on other anatomical structures, various other electrode placements may be employed, such as, for example, focusing on nerve block sites known to be used in connection with anesthetizing those anatomical structures upon which surgery has been performed.

Although the invention has been described with reference to a particular arrangement of parts, features and the like, these are not intended to exhaust all possible arrangements or features, and indeed many other modifications and variations will be ascertainable to those of skill in the art.

What is claimed is:

1. An interferential current therapy kit for treatment of a patient following an orthopedic surgery, said kit comprising, within a container for facilitating the distribution and transport of said kit, the following:
a plurality of electrodes configured to be disposed on an epidermis of the patient and arranged to supply transcutaneous electrical impulses to a therapeutic target area when supplied with power, wherein said plurality of electrodes comprises at least two electrodes adapted to supply transcutaneous electrical impulses at two different frequencies, the transcutaneous electrical impulses provided at two different frequencies adapted to give rise to at least one beat impulse having an interference frequency;
an interferential current therapy control unit comprising a stimulation power supply in electrical communication with said plurality of electrodes, said interferential current therapy control unit configured to supply interferential current electrical impulses at the two different frequencies to the at least two electrodes in order to generate the transcutaneous electrical impulses giving rise to the at least one beat impulse; and
an electrode placement aid adapted to assist the patient with placement of said plurality of electrodes with respect to a site of the previous orthopedic surgery, thereby increasing a likelihood of efficacious placement of said plurality of electrodes.

2. The interferential current therapy kit of claim 1, wherein said electrode placement aid comprises a marking instrument.

3. The interferential current therapy kit of claim 2, wherein the marking instrument comprises an ink marker.

4. The interferential current therapy kit of claim 1, wherein said electrode placement aid comprises a template.

5. The interferential current therapy kit of claim 4 wherein the template comprises a drape that includes at least one of openings and markings showing a relative intended placement of said plurality of electrodes with respect to anatomical structure.

6. The interferential current therapy kit of claim 1, wherein said electrode placement aid comprises a measuring device.

7. The interferential current therapy kit of claim 6, wherein the measuring device comprises at least one of a ruler and a tape measure.

8. The interferential current therapy kit of claim 1, wherein said electrode placement aid comprises an x-ray marker.

9. The interferential current therapy kit of claim 8, wherein the x-ray marker comprises at least one of the following: radiology tape with metal beads, radiology tape with a central strip of radiopaque marker and other radiology devices which are radiopaque, but are not metallic in nature.

10. The interferential current therapy kit of claim 1, wherein said electrode placement aid comprises an imaging device adapted to assist with electrode placement.

11. The interferential current therapy kit of claim 10, wherein the imaging device is adapted to interface with a mobile phone or tablet.

12. The interferential current therapy kit of claim 1, wherein said electrode placement aid is adapted to interface with markings created on a body of the patient.

13. The interferential current therapy kit of claim 1, wherein said control unit further comprises at least one sensor adapted to provide sensor feedback indicative of a patient parameter derived from the patient.

14. The interferential current therapy kit of claim 1, further comprising a plurality of wire leads adapted to connect said control unit with said plurality of electrodes.

15. The interferential current therapy kit of claim 1, wherein said plurality of electrodes comprises:
a first electrode adapted to supply transcutaneous electrical impulses at a first frequency and a second electrode adapted to supply transcutaneous electrical impulses at a second frequency different than the first frequency, the transcutaneous electrical impulses provided at the first and second frequencies adapted to give rise to a first beat impulse having a first interference frequency; and a third electrode adapted to supply transcutaneous electrical impulses at a third frequency and a fourth electrode adapted to supply transcutaneous electrical impulses at a fourth frequency different than the third frequency, the transcutaneous electrical impulses provided at the third and fourth frequencies adapted to give rise to a second beat impulse having a second interference frequency.

16. An interferential current therapy kit for treatment of a patient following an orthopedic surgery, said kit comprising:
a plurality of electrodes configured to be disposed on an epidermis of the patient and arranged to supply transcutaneous electrical impulses to a therapeutic target area when supplied with power, wherein said plurality of electrodes comprises at least two electrodes adapted to supply transcutaneous electrical impulses at two different frequencies, the transcutaneous electrical impulses provided at two different frequencies adapted to give rise to at least one beat impulse having an interference frequency;
an interferential current therapy control unit comprising a stimulation power supply in electrical communication with said plurality of electrodes, said interferential current therapy control unit configured to supply interferential current electrical impulses at the two different frequencies to the at least two electrodes in order to generate the transcutaneous electrical impulses giving rise to the at least one beat impulse; and
an electrode placement aid adapted to assist the patient with placement of said plurality of electrodes with respect to a site of the previous orthopedic surgery, said electrode placement aid comprising at least one of the following:
a marking instrument;
a template;
a measuring device;
an x-ray marker; and
an imaging device.

17. The interferential current therapy kit of claim 16, wherein said electrode placement aid comprising at least two of the following:
a marking instrument;
a template;
a measuring device;
an x-ray marker; and
an imaging device.

18. The interferential current therapy kit of claim 17, wherein said electrode placement aid comprising at least three of the following:
a marking instrument;
a template;
a measuring device;
an x-ray marker; and
an imaging device.

19. The interferential current therapy kit of claim 16, wherein said control unit further comprises at least one sensor adapted to provide sensor feedback indicative of a patient parameter derived from the patient.

20. The interferential current therapy kit of claim 16, wherein said plurality of electrodes comprises:
a first electrode adapted to supply transcutaneous electrical impulses at a first frequency and a second electrode adapted to supply transcutaneous electrical impulses at a second frequency different than the first frequency, the transcutaneous electrical impulses provided at the first and second frequencies adapted to give rise to a first beat impulse having a first interference frequency; and
a third electrode adapted to supply transcutaneous electrical impulses at a third frequency and a fourth electrode adapted to supply transcutaneous electrical impulses at a fourth frequency different than the third frequency, the transcutaneous electrical impulses provided at the third and fourth frequencies adapted to give rise to a second beat impulse having a second interference frequency.

21. An interferential current therapy kit for treatment of a patient following an orthopedic surgery, said kit comprising, within a container for facilitating the distribution and transport of said kit, the following:
a control unit comprising a stimulation power supply;
a plurality of electrodes configured to be in electrical communication with the stimulation power supply, said plurality of electrodes configured to be disposed on an epidermis of the patient and arranged to supply transcutaneous electrical impulses to a therapeutic target area when supplied power by said stimulation power supply, wherein said plurality of electrodes comprises at least two electrodes adapted to supply transcutaneous electrical impulses at two different frequencies, the transcutaneous electrical impulses provided at two different frequencies adapted to give rise to at least one beat impulse having an interference frequency; and
an electrode placement aid adapted to assist the patient with placement of said plurality of electrodes with respect to a site of the previous orthopedic surgery, thereby increasing a likelihood of efficacious placement of said plurality of electrodes;
wherein said plurality of electrodes comprises:
a first electrode adapted to supply transcutaneous electrical impulses at a first frequency and a second electrode adapted to supply transcutaneous electrical impulses at a second frequency different than the first frequency, the transcutaneous electrical impulses provided at the first and second frequencies adapted to give rise to a first beat impulse having a first interference frequency; and
a third electrode adapted to supply transcutaneous electrical impulses at a third frequency and a fourth electrode adapted to supply transcutaneous electrical impulses at a fourth frequency different than the third frequency, the transcutaneous electrical impulses provided at the third and fourth frequencies adapted to give rise to a second beat impulse having a second interference frequency.

22. An interferential current therapy kit for treatment of a patient following an orthopedic surgery, said kit comprising:
a control unit comprising a stimulation power supply;
a plurality of electrodes configured to be in electrical communication with the stimulation power supply, said plurality of electrodes configured to be disposed on an epidermis of the patient and arranged to supply transcutaneous electrical impulses to a therapeutic target area when supplied power by said stimulation power supply, wherein said plurality of electrodes comprises at least two electrodes adapted to supply transcutaneous electrical impulses at two different frequencies, the transcutaneous electrical impulses provided at two different frequencies adapted to give rise to at least one beat impulse having an interference frequency; and an electrode placement aid adapted to assist the patient with placement of said plurality of electrodes with respect to a site of the previous orthopedic surgery, said electrode placement aid comprising at least one of the following:
a marking instrument;
a template;
a measuring device;
an x-ray marker; and
an imaging device;
wherein said plurality of electrodes comprises:
a first electrode adapted to supply transcutaneous electrical impulses at a first frequency and a second electrode adapted to supply transcutaneous electrical impulses at a second frequency different than the first frequency, the transcutaneous electrical impulses provided at the first and second frequencies adapted to give rise to a first beat impulse having a first interference frequency; and
a third electrode adapted to supply transcutaneous electrical impulses at a third frequency and a fourth electrode adapted to supply transcutaneous electrical impulses at a fourth frequency different than the third frequency, the transcutaneous electrical impulses provided at the third and fourth frequencies adapted to give rise to a second beat impulse having a second interference frequency.

* * * * *